(12) United States Patent
Ma

(10) Patent No.: US 10,121,559 B2
(45) Date of Patent: Nov. 6, 2018

(54) HEALTH CONDITION ALARM SYSTEM

(71) Applicant: Richard Ma, Carlisle, MA (US)

(72) Inventor: Richard Ma, Carlisle, MA (US)

( * ) Notice: Subject to any disclaimer, the term of this patent is extended or adjusted under 35 U.S.C. 154(b) by 0 days.

(21) Appl. No.: 15/285,164

(22) Filed: Oct. 4, 2016

(65) Prior Publication Data

US 2017/0098050 A1    Apr. 6, 2017

Related U.S. Application Data

(60) Provisional application No. 62/237,036, filed on Oct. 5, 2015.

(51) Int. Cl.
| | |
|---|---|
| *G16H 40/63* | (2018.01) |
| *G08B 21/04* | (2006.01) |
| *G08B 25/10* | (2006.01) |
| *G06F 19/00* | (2018.01) |
| *G08B 25/00* | (2006.01) |

(52) U.S. Cl.
CPC ............ *G16H 40/63* (2018.01); *G06F 19/00* (2013.01); *G08B 21/0453* (2013.01); *G08B 25/009* (2013.01); *G08B 25/10* (2013.01)

(58) Field of Classification Search
CPC .... G16H 40/63; G06F 19/00; G08B 21/0453; G08B 25/009; G08B 25/10
See application file for complete search history.

(56) References Cited

U.S. PATENT DOCUMENTS

| | | | |
|---|---|---|---|
| 8,419,660 B1 * | 4/2013 | Shaw ................... | A47C 31/123 600/587 |
| 2009/0243878 A1 * | 10/2009 | Ricordi ................ | A61B 5/0002 340/870.16 |

* cited by examiner

*Primary Examiner* — Leon Flores
(74) *Attorney, Agent, or Firm* — Polsinelli, PC

(57) ABSTRACT

A patient and health condition monitoring system comprising:
 a treatment device;
 a condition monitor;
 a patient care controller, the patient care controller comprising:
  a signal receiver;
  a healthcare professional database;
  a processing element coupled to the healthcare professional database; and
 an alarm generator.

15 Claims, 2 Drawing Sheets

HEALTH CONDITION ALARM SYSTEM

RELATED APPLICATIONS

This application claims the benefit of priority to U.S. Provisional application Ser. No. 62/237,036 filed Oct. 5, 2015, the disclosure of which is incorporated herein by reference as if fully set forth in its entirety.

SUMMARY OF THE INVENTION

In accordance with the invention there is provided a patient and health condition monitoring system (10) comprising:

a treatment device (20) being utilized to treat a patient at a first location, the treatment device including one or more sensors configured to detect and transmit one or more monitoring signals indicating an operational status of the treatment device;

a condition monitor (30) coupled to the treatment device, the condition monitor configured to receive and analyze the one or more monitoring signals from the treatment device in order to identify one or more abnormal operational conditions, and in response generate and transmit an alert signal (32) indicative of the one or more abnormal operational conditions;

a patient care controller (40), the patient care controller comprising:

a signal receiver (42) configured to receive the alert signal from the condition monitor;

a healthcare professional database (44) configured to provide information associated with a plurality of healthcare professionals and a respective one or more communication devices (50) that may be used to communicate with a given healthcare professional;

a processing element coupled to the healthcare professional database, the processing element configured to analyze the alert signal and determine at least one suitable healthcare professional for responding to the alert signal and further determine a suitable communication device for communicating with the suitable healthcare professional; and an alarm generator configured to automatically generate an alarm signal (4) and transmit the alarm signal to the suitable communication device for the suitable healthcare professional.

In such a system the patient care controller is typically provided by a server (44) using Internet Protocol (IP) to communicate with one or more of the treatment device, the condition monitor, and the one or more communication devices, the server located at a second location remote from the first location and Internet Protocol used for performing the transmitting and receiving.

The patient care controller is preferably provided by a cellular tower (80) using radio communication (32a, 82) to communicate with one or more of the treatment device, the condition monitor, and the one or more communication devices, the cellular tower located a second location remote from the first location and radio communication used for performing the transmitting and receiving The patient care controller is preferably coupled to the treatment device and is provided at the first location in close proximity to the condition monitor, the patient care controller being configured to transmit the alarm signal to the suitable communication device for the suitable healthcare professional using Bluetooth or a Personal Area Network (PAN).

The alarm signal typically comprises one or more of a patient identifier, a treatment device identifier, a treatment location, one or more of the abnormal operational conditions, and an operational history of the treatment device.

Each communication device typically further comprises a physical alarm device, the physical alarm device configured to receive the alarm signal and automatically trigger one or more of a visual alarm (5), an auditory alarm (6), or a haptic alarm (6).

The patient care controller is preferably further configured to transmit the alarm signal to each of the one or more communication devices that may be used to communicate with the suitable healthcare professional.

Typically, an abnormal operational condition is indicated by an operational status of the treatment device that passes a threshold value or falls outside of an expected range of values.

In another aspect of the invention there is provided a method for monitoring a patient or health condition, the method comprising the steps of:

detecting and transmitting one or more monitoring signals indicating an operational status of a treatment device (20) being used to treat a patient at a first location, the treatment device including one or more sensors configured to perform the detecting and transmitting;

receiving and analyzing the one or more monitoring signals from the treatment device in order to identify one or more abnormal operating conditions of the treatment device, the receiving and analyzing performed by a condition monitor (30);

in response to identifying one or more abnormal operating conditions, causing the condition monitor to generate and transmit an alert signal (32) indicative of the one or more abnormal operational conditions;

receiving the alert signal from the condition monitor at a patient controller (40) and analyzing the alert signal against a healthcare professional database (44) containing information associated with a plurality of healthcare professionals in order to determine at least one suitable healthcare professional for responding to the alert signal;

analyzing the alert signal to determine a suitable communication device (50) for communicating with the suitable healthcare professional;

automatically generating an alarm signal (4) and transmitting the alarm signal to the suitable communication device.

Such a method preferably further comprises providing the patient controller at a second location remote from the first location and using one or more of a server (44) and Internet Protocol (IP), and a cellular tower (80) and mobile radio communication (32a, 82), to perform the transmitting and receiving.

Such a method can further comprise providing the patient controller at the first location and using one or more of the communication devices and Bluetooth or Personal Area Networks (PANs) to perform the transmitting and receiving.

In such a method the alarm signal can comprise one or more of a patient identifier, a treatment device identifier, a treatment location, one or more of the abnormal operational conditions, and an operational history of the treatment device.

Such a method can further comprise notifying the suitable healthcare professional of the alarm signal by receiving the alarm signal at a physical alarm device of the suitable communication device and automatically triggering one or more of a visual alarm (5), an auditory alarm (6), or a haptic alarm (6).

Such a method can further comprise transmitting the alarm signal to each of a plurality of communication devices that can be used to communicate with the suitable healthcare professional.

In such a method, the step of identifying one or more abnormal operational conditions typically comprises determining that the operational status of the treatment device has passed a threshold value or falls outside of an expected range of values.

DETAILED DESCRIPTION OF THE INVENTION

Figure 3:
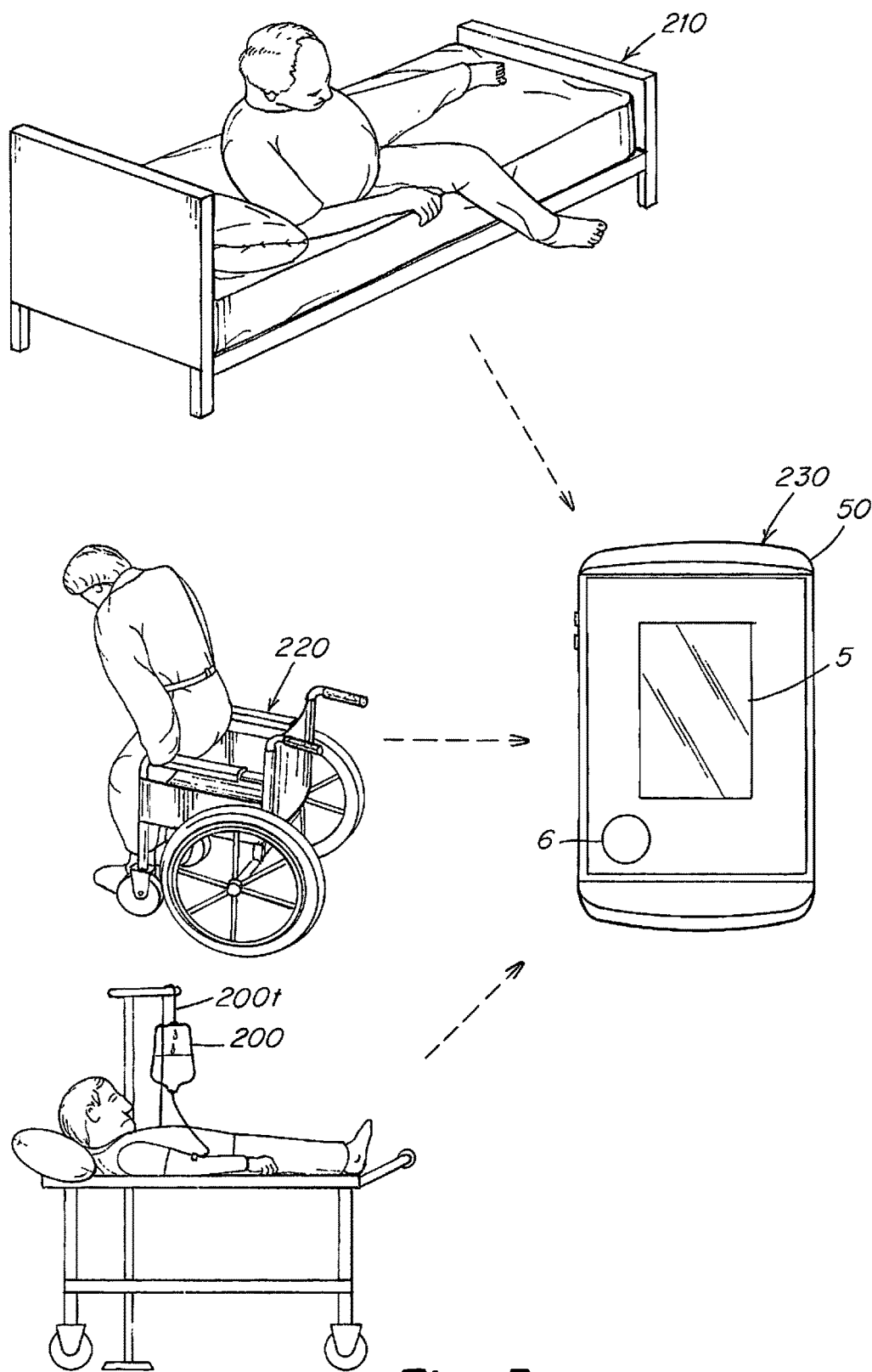
FIG. 3 is a schematic views of a variety of environments and devices that a health care patient is typically associated with in a hospital or health care facility where the devices include a monitor and signal generator that sends a signal to a device in the possession of a health care provider in a remote location, the signal activating an alert or alarm contained within the device such as a cell phone.

The present invention comprises a system and method that sends an alarm signal to a health care provider or attendant such as a medical nurse or doctor at a location remote from the room or location where a patient who is being watched or treated is located. The alarm signal that is sent alerts the health care provider that a device that is providing the patient with some sort of care has reached a state or condition that requires attention to the device or the patient. As shown in FIG. 3, such devices 20 can include for example an intravenous fluid delivery device or IV pump 200, a bed 210, a chair 220.

The device that is providing the patient with the subject care is preferably equipped with a sensor that detects when the device has reached a state or condition that requires attention to the patient. In the case of an IV pump 200, the condition to be monitored can be that the fluid to be delivered to the patient has stopped flowing through the tubing 200t that is connected to the patient such as when the pump gets clogged or the supply of fluid runs out. In the case of a chair 220, the condition can be that the patient has gotten out of the chair and is no longer sitting completely on the seat. In the case of a bed 210, the condition can be that the patient has gotten out of the bed or is otherwise not completely lying on the mattress of the bed.

Figure 1:
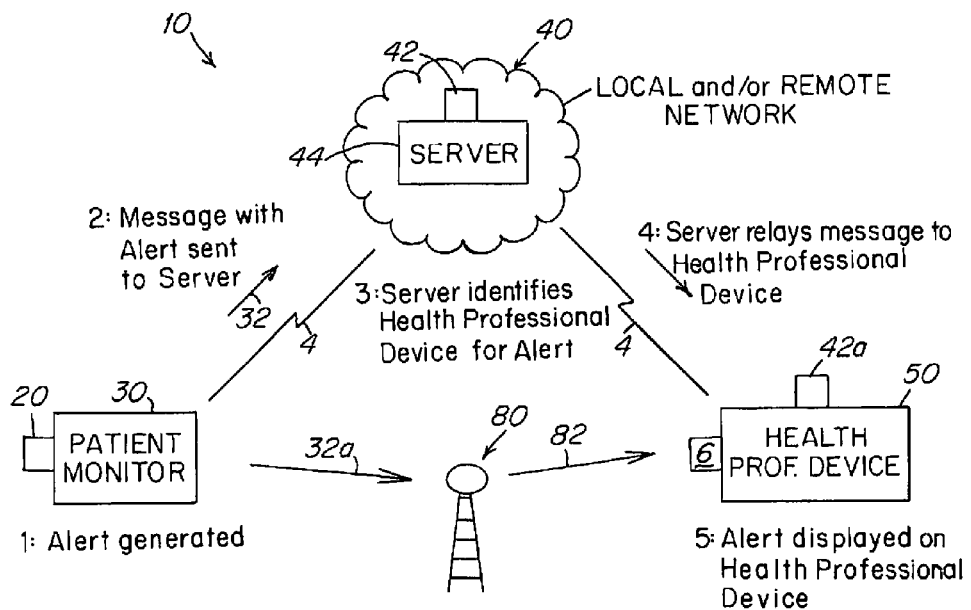
FIG. 1 is a schematic view of various embodiments of a communications network by which a health care patient monitor can send status or alarm signals to a remotely located wireless router and data processing server that in turn sends status or alarm signals to a device in the possession or vicinity of a health care provider, the device including an alarm or alert generator that is activated on receipt of the status or alarm signal.
Figure 2:
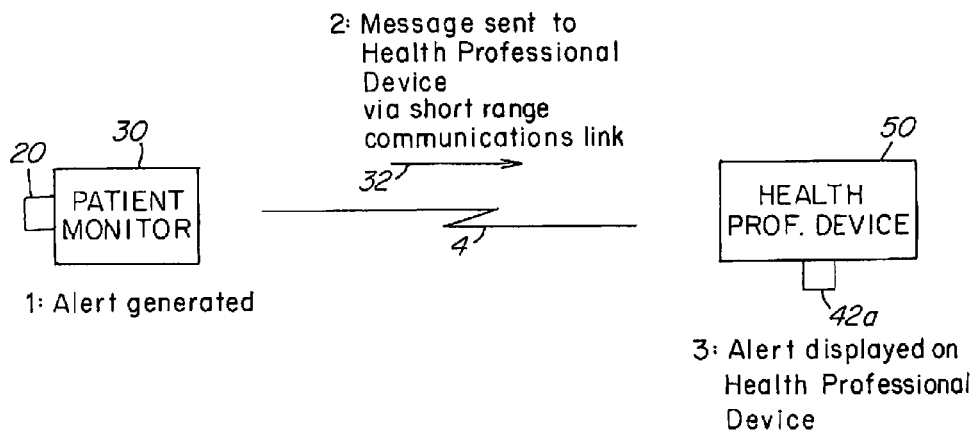
FIG. 2 is a schematic view of a health care patient monitor that can send status or alarm signals to a remotely located cell phone signal receiving and sending tower that in turn sends status or alarm signals to a cell phone or other device in the possession or vicinity of a health care provider, the device including an alarm or alert generator that is activated on receipt of the status or alarm signal.

The device to be monitored, 20, FIGS. 1, 2 is interconnected to a condition monitor 30 that includes a chip or other signal sending device that both detects a preselected condition of the device 20 and sends an electronic or electromagnetic signal 32 to a signal receiver 42 located in a location remote from the room or location where the patient is located such as a nursing station or a cell phone 230 that is remote from the patient's room. The remotely located signal receiver 42 sends or generates a message to or on a device 50 in the possession or immediate vicinity of the health care provider or activates an alarm on the device 50 that the health care provider is certain to notice. For example, the remote signal receiver 42 can be a receiver contained in a cell phone 230 that is carried by a nurse or a wireless router located within normal wireless router range of the location of patients' rooms in a hospital (typically anywhere from about 1-150 feet) or a cellular phone signal tower located outside the hospital building.

Once the signal receiver 42 receives the signal from the chip or other signal sending device 20, the signal receiver 42 either sends an electronic message to or activates an alarm contained in a device 50 that the health care provider is either carrying on their person or is located in a location remote from the room where the patient is located at which the health care provider is normally expected to be located while on duty such as a nursing station.

The chip or other signal sending device 20 is programmed to include signal information that identifies the patient themselves or the location of the patient such as room number and preferably also the identity of the device 30 that is being monitored and also preferably the identity of the condition of the device 30 that is being monitored.

In one embodiment, all staff on the floor of a health care facility, can receive a text message on their cell phone 230 of the occurrence of the preselected condition of the device 30 being monitored. The primary nurse assigned to taking care of the patient can receive an alarm signal such as beeping or flashing light on the nurse's cell phone. Once any of the staff takes care of the issue the alarm on the primary nurse's phone will shut off and the text message will be acknowledged. Unlike the present state of health care systems where devices such as IV pumps, beds and chairs set off an alarm contained mounted on or to the device itself located within the patient's room, such a system as described herein will:

1. Improve patient care as everyone can work together to prevent medications from running out or prevent patients from not getting medications when their IV is clogged.

2. Provide a faster more efficient way to prevent falls by elderly and confused (demented) patients in the hospital.

3. Eliminate or significantly reduce the sound of loud noises from alarms mounted on or to pumps, beds or chairs that wake patients up or otherwise keep patients from sleeping which is essential to healing and recovery.

4. Serve to reduce or prevent delirium as many elderly patients can get confused when they can't sleep leading to increased mortality.

5. Reduce or prevent potential disputes of malfeasance or malpractice.

6. Improve patient satisfaction scores.

When patients are already confused or demented they can't process an IV alarm and call staff to take care of issues leading to possible complications if they can't get their intended medications through their IV pump. Currently when a patient's IV pole is not working, they are expected to ring a call bell to call a secretary on the floor who then pages the patient's nurse to take care of the issue.

Current health care systems reward doctors and hospitals for high patient satisfaction scores. If a patient's IV pole alarms and it takes a long time for a nurse to respond then the perception among patients and families is that they are getting neglected and getting poor care.

In one embodiment as shown in FIG. 1, the signal generator 20 can generate a long range signal such as an RF frequency signal that can travel typically from about 1 to about 300 feet to a signal receiver 42. In such an embodiment the remote signal receiver can comprise a wireless router 42 interconnected to an email or text message server 44 that includes programming and intelligence sufficient to identify the condition of the monitor 30 and preferably the location of the monitor 30 or the identity of the patient associated with the monitor 30. The wireless router 42 is located remotely from the room in which the patient and patient monitor 30 are located, typically at least about 10-200 feet away from the location of the patient. The server 44 receives the signal 32 via the router 44 and is programmed to automatically sends an alert or alarm signal 4 to the device 50. The device 50 includes a signal receiver 42a that receives the signal 4 and activates one or more alert mechanisms such as a speaker 6 or vibrator 6 or a visual display 5 contained within the device 50. A typical visual display mechanism is a text message display 5 on a cell phone or an email 5 that is displayed on a monitor to a laptop or PC located at a nursing station. The server 44 can be programmed to send the signal 4 or multiple signals 4 to multiple devices 50 such as to one or more cell phones and one or more servers located at one or more nursing stations. The device 50 can receive the signal 4 from the server 44 wirelessly from the router 42 or via a hard wired connection between the server 44 and the device 50.

In another embodiment of the invention, FIG. 1, the signal sending device can comprise a cell phone signal generator that communicates a signal 32a with or to a remotely located cell phone system tower 80 that automatically upon receipt of signal 32a sends a cell phone signal 82 to the signal receiver 42a of the device 50 such as a cell phone in the possession or vicinity of the health care provider. The tower 80 is typically located in a very distant physical location relative to the room in which the patient is located such as between about 100 feet and about 20 miles away from the location of the patient. Again, the signal receiver 42a that receives the signal 82 can activate one or more alert mechanisms such as a speaker 6 or vibrator 6 or a visual display 5 contained within the device 50, FIGS. 1-3.

In another embodiment of the invention, FIG. 2 the chip or other signal sending device 20 can send a signal 32 such as a blue tooth signal directly to a signal receiver 42a that is mounted or contained within the device or devices 50 that generate the alert or alarm 3 that is generated by or displayed on the remote device 50. In such an embodiment the device 50 contains a program or circuit that processes the received signal 32 to cause the alert or alarm or message 3 to be generated or displayed on the device 50.

What is claimed is:

1. A patient and health condition monitoring system comprising:
   a treatment device being utilized to treat a patient at a first location, the treatment device including one or more sensors configured to detect and transmit one or more monitoring signals indicating an operational status of the treatment device;
   a condition monitor coupled to the treatment device, the condition monitor configured to receive and analyze the one or more monitoring signals from the treatment device in order to identify one or more abnormal operational conditions, and in response generate and transmit an alert signal indicative of the one or more abnormal operational conditions;
   a patient care controller, the patient care controller comprising:
      a signal receiver configured to receive the alert signal from the condition monitor;
      a healthcare professional database configured to provide information associated with a plurality of healthcare professionals and a respective one or more communication devices that may be used to communicate with a given healthcare professional;
      a data processing server coupled to the healthcare professional database, the data processing server configured to analyze the alert signal and determine at least one suitable healthcare professional for responding to the alert signal and further determine a suitable communication device for communicating with the suitable healthcare professional; and
      an alarm generator configured to automatically generate an alarm signal and transmit the alarm signal to the suitable communication device for the suitable healthcare professional.

2. The patient and health condition monitoring system as claimed in claim 1, wherein the patient care controller is provided by a server using Internet Protocol (IP) to communicate with one or more of the treatment device, the condition monitor, and the one or more communication devices, the server located at a second location remote from the first location and Internet Protocol used for performing the transmitting and receiving.

3. The patient and health condition monitoring system as claimed in claim 1, wherein the patient care controller is provided by a cellular tower using radio communication to communicate with one or more of the treatment device, the condition monitor, and the one or more communication devices, the cellular tower located a second location remote from the first location and radio communication used for performing the transmitting and receiving.

4. The patient and health condition monitoring system as claimed in claim 1, wherein the patient care controller is coupled to the treatment device and is provided at the first location in close proximity to the condition monitor, the patient care controller being configured to transmit the alarm signal to the suitable communication device for the suitable healthcare professional using Bluetooth or a Personal Area Network (PAN).

5. The patient and health condition monitoring system as claimed in claim 1, wherein the alarm signal comprises one or more of a patient identifier, a treatment device identifier, a treatment location, one or more of the abnormal operational conditions, and an operational history of the treatment device.

6. The patient and health condition monitoring system as claimed in claim 1, wherein each communication device further comprises a physical alarm device, the physical alarm device configured to receive the alarm signal and automatically trigger one or more of a visual alarm, an auditory alarm, or a haptic alarm.

7. The patient and health condition monitoring system as claimed in claim 1, wherein the patient care controller is further configured to transmit the alarm signal to each of the one or more communication devices that may be used to communicate with the suitable healthcare professional.

8. The patient and health condition monitoring system as claimed in claim 1, wherein an abnormal operational condition is indicated by an operational status of the treatment device that passes a threshold value or falls outside of an expected range of values.

9. A method for monitoring a patient or health condition, the method comprising the steps of:
- detecting and transmitting one or more monitoring signals indicating an operational status of a treatment device being used to treat a patient at a first location, the treatment device including one or more sensors configured to perform the detecting and transmitting;
- receiving and analyzing the one or more monitoring signals from the treatment device in order to identify one or more abnormal operating conditions of the treatment device, the receiving and analyzing performed by a condition monitor;
- in response to identifying one or more abnormal operating conditions, causing the condition monitor to generate and transmit an alert signal indicative of the one or more abnormal operational conditions;
- receiving the alert signal from the condition monitor at a patient controller and analyzing the alert signal against a healthcare professional database containing information associated with a plurality of healthcare professionals in order to determine at least one suitable healthcare professional for responding to the alert signal;
- analyzing the alert signal to determine a suitable communication device for communicating with the suitable healthcare professional;
- automatically generating an alarm signal and transmitting the alarm signal to the suitable communication device.

10. The method for monitoring a patient or health condition as claimed in claim 9, further comprising providing the patient controller at a second location remote from the first location and using one or more of a server and Internet Protocol (IP), and a cellular tower and mobile radio communication, to perform the transmitting and receiving.

11. The method for monitoring a patient or health condition as claimed in claim 9, further comprising providing the patient controller at the first location and using one or more of the communication devices and Bluetooth or Personal Area Networks (PANs) to perform the transmitting and receiving.

12. The method for monitoring a patient or health condition as claimed in claim 9, wherein the alarm signal comprises one or more of a patient identifier, a treatment device identifier, a treatment location, one or more of the abnormal operational conditions, and an operational history of the treatment device.

13. The method for monitoring a patient or health condition as claimed in claim 9, further comprising notifying the suitable healthcare professional of the alarm signal by receiving the alarm signal at a physical alarm device of the suitable communication device and automatically triggering one or more of a visual alarm, an auditory alarm, or a haptic alarm.

14. The method for monitoring a patient or health condition as claimed in claim 9, further comprising transmitting the alarm signal to each of a plurality of communication devices that can be used to communicate with the suitable healthcare professional.

15. The method for monitoring a patient or health condition as claimed in claim 9, wherein identifying one or more abnormal operational conditions comprises determining that the operational status of the treatment device has passed a threshold value or falls outside of an expected range of values.

* * * * *